(12) United States Patent
Kanamori et al.

(10) Patent No.: US 7,468,342 B2
(45) Date of Patent: Dec. 23, 2008

(54) CATALYSTS AND PROCESS FOR PRODUCING AROMATIC AMINES

(75) Inventors: Yoshinori Kanamori, Niigata (JP); Shuji Ebata, Niigata (JP); Kengo Tsukahara, Niigata (JP); Yasushi Hiramatsu, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/139,214

(22) Filed: May 7, 2002

(65) Prior Publication Data

US 2002/0177735 A1 Nov. 28, 2002

(30) Foreign Application Priority Data

May 22, 2001 (JP) ............................. 2001-152012
May 22, 2001 (JP) ............................. 2001-152013

(51) Int. Cl.
*B01J 23/00* (2006.01)
*B01J 21/00* (2006.01)
*B01J 20/00* (2006.01)

(52) U.S. Cl. ..................... 502/327; 502/242; 502/259; 502/260; 502/314; 502/315; 502/335; 502/337; 502/349; 502/407; 502/415; 502/439

(58) Field of Classification Search ................ 502/242, 502/259, 260, 314, 315, 335, 337, 349, 350, 502/351, 439, 308, 327, 415, 407
See application file for complete search history.

(56) References Cited

U.S. PATENT DOCUMENTS

| | | | | |
|---|---|---|---|---|
| 3,926,853 A | * | 12/1975 | Senes et al. ................. 252/456 |
| 3,988,262 A | * | 10/1976 | Andersen et al. ............. 502/335 |
| 4,009,194 A | * | 2/1977 | Umemura et al. ........... 558/324 |
| 4,031,106 A | * | 6/1977 | DelPesco ..................... 546/311 |
| 4,197,217 A | * | 4/1980 | Gartshore et al. ........... 502/314 |
| 4,307,248 A | | 12/1981 | Barnett et al. |
| 4,342,698 A | * | 8/1982 | Bartek et al. ................. 549/505 |
| 4,499,209 A | * | 2/1985 | Hoek et al. ................... 518/707 |
| 4,522,939 A | * | 6/1985 | Minderhoud et al. ........ 502/242 |
| 4,528,398 A | * | 7/1985 | Callahan et al. ............. 562/534 |
| 4,628,130 A | * | 12/1986 | Bournonville et al. ....... 568/885 |
| 4,637,993 A | * | 1/1987 | Van Erp et al. ............. 502/242 |
| 4,668,654 A | * | 5/1987 | Drake .......................... 502/242 |
| 4,670,416 A | * | 6/1987 | Klimmek et al. ............. 502/259 |
| 4,681,867 A | * | 7/1987 | Dyer et al. ................... 502/242 |
| 4,829,040 A | * | 5/1989 | Ward ........................... 502/206 |
| 4,857,497 A | * | 8/1989 | De Jong et al. .............. 502/242 |
| 4,857,499 A | * | 8/1989 | Ito et al. ....................... 502/326 |
| 4,956,328 A | * | 9/1990 | Frohning et al. ............. 502/242 |
| 4,962,078 A | * | 10/1990 | Behrmann et al. ........... 502/325 |
| 4,977,126 A | * | 12/1990 | Mauldin et al. .............. 502/242 |
| 5,068,468 A | | 11/1991 | Schossig et al. |
| 5,082,816 A | * | 1/1992 | Teller et al. .................... 502/84 |
| 5,112,792 A | * | 5/1992 | Lok ............................. 502/250 |
| 5,169,821 A | * | 12/1992 | Soled et al. .................. 502/242 |
| 5,217,938 A | * | 6/1993 | Reinalda et al. ............. 502/325 |
| 5,312,795 A | * | 5/1994 | Kaminsky et al. ........... 502/174 |
| 5,320,998 A | * | 6/1994 | Horiuchi ...................... 502/245 |
| 5,352,835 A | * | 10/1994 | Dai et al. ..................... 564/480 |
| 5,356,847 A | * | 10/1994 | Henderson ................... 502/84 |
| 5,595,719 A | * | 1/1997 | Ul-Haque et al. ........ 423/418.2 |
| 5,635,439 A | * | 6/1997 | Fukui et al. ................. 502/328 |
| 5,736,484 A | | 4/1998 | Polanek et al. |
| 5,744,419 A | * | 4/1998 | Choudhary et al. ......... 502/326 |
| 5,916,838 A | * | 6/1999 | Wulff-Doring et al. ...... 502/326 |
| 5,958,825 A | * | 9/1999 | Wulff-Doring et al. ...... 502/300 |
| 6,034,029 A | * | 3/2000 | Wulff-Doring et al. ...... 502/308 |
| 6,117,814 A | * | 9/2000 | Plecha et al. ................. 502/325 |
| 6,140,539 A | | 10/2000 | Sander et al. |
| 6,235,677 B1 | * | 5/2001 | Manzer et al. ............... 502/232 |

(Continued)

FOREIGN PATENT DOCUMENTS

DE 199 09 176 A1 9/2000

(Continued)

OTHER PUBLICATIONS

Partial European Search Report, mailed Sep. 6, 2002, for EP 02 01 0805.

*Primary Examiner*—Cam N. Nguyen
(74) *Attorney, Agent, or Firm*—Antonelli, Terry, Stout & Kraus, LLP.

(57) ABSTRACT

As catalysts for producing aromatic amines by hydrogenating aromatic nitriles, there are disclosed (1) the catalyst comprising a metal catalyst component comprising Ni and/or Co and a specific amount of zirconia as a carrier component, which is prepared by drying, calcining and forming a precipitate produced by adding an aqueous solution containing soluble salts of the metal catalyst component and the carrier component to an aqueous alkali solution; and (2) the catalyst comprising the metal catalyst component and the carrier component, which is prepared by filtering a precipitate produced by adding an aqueous solution containing soluble salts of the metal catalyst component and the carrier component to an aqueous alkali solution; forming the precipitate without drying to obtain a formed product; and subjecting the formed product to drying and then calcining. These catalysts are free from breaking owing to rapid generation of methane and evaporation of liquid ammonia by hydrogenolysis of high boiling by-products of the hydrogenation when reactivated after deactivation of the catalyst, which allows the long-term use of the catalysts.

21 Claims, No Drawings

U.S. PATENT DOCUMENTS

| | | | |
|---|---|---|---|
| 6,242,380 B1 * | 6/2001 | Park et al. | 502/337 |
| 6,245,709 B1 * | 6/2001 | Clark et al. | 502/326 |
| 6,521,564 B2 * | 2/2003 | Degischer et al. | 502/301 |
| 6,524,994 B1 * | 2/2003 | Reesink et al. | 502/337 |
| 6,677,271 B1 * | 1/2004 | Birke et al. | 502/337 |
| 6,693,060 B2 * | 2/2004 | Park et al. | 502/337 |
| 6,777,371 B2 * | 8/2004 | Liu | 502/337 |
| 6,787,118 B2 * | 9/2004 | Roark et al. | 423/247 |

FOREIGN PATENT DOCUMENTS

| | | |
|---|---|---|
| DE | 199 09 177 A1 | 9/2000 |
| EP | 0614692 A1 * | 9/1994 |
| EP | 1 163 955 A1 | 12/2001 |

* cited by examiner

CATALYSTS AND PROCESS FOR PRODUCING AROMATIC AMINES

BACKGROUND OF THE INVENTION

1. Field of the Invention

The present invention relates to catalysts for hydrogenating aromatic nitrites into aromatic amines, and a process for producing aromatic amines using such catalysts. The aromatic amines produced according to the present invention are useful as raw materials for curing agents, synthetic resins, isocyanates and the like.

2. Background Art

There have been proposed various metal catalyst systems for hydrogenating aromatic nitrites. For example, Japanese Patent Application Laid-Open No. 51-101930 discloses a process for producing benzylamines and dibenzylamines by hydrogenating benzonitriles or isophthalonitriles. This process employs a catalyst system composed of Raney nickel in pellet form, zirconium supported on diatomaceous earth in tablet form, reduced nickel co-catalyst, and platinum supported on alumina in tablet form. Further, Japanese Patent Application Laid-Open No. 62-129257 discloses a process for producing benzylamines by hydrogenating benzonitriles in the coexistence of ammonia using Raney nickel or Raney cobalt. Japanese Patent Application Laid-Open No. 5-97776 discloses, in Examples thereof, a process for producing benzylamines by hydrogenating benzonitriles using a cobalt-alumina catalyst. Japanese Patent Application Laid-Open Nos. 9-40630 and 10-204048 disclose a process for producing aromatic cyanomethylamines by hydrogenating only one of two nitrile groups of aromatic dinitrile in the presence of Raney catalyst containing nickel and/or cobalt.

These hydrogenation processes have the advantage that the aromatic amines are produced in high yield. In any of these processes, however, high boiling by-products of the hydrogenation adhere to the catalyst, thereby decreasing the yield of desired amine product. When such high boiling by-products undergo hydrogenolysis in order to reactivate the deactivated catalyst, the catalyst ruptures owing to rapid generation of methane and evaporation of liquid ammonia, which results in an increase in pressure differential in the reaction system, and extremely short lifetime of the catalyst.

SUMMARY OF THE INVENTION

It is therefore an object of the present invention to provide a catalyst for hydrogenating aromatic nitrites into aromatic amines, which is free from breaking owing to rapid generation of methane and evaporation of liquid ammonia by hydrogenolysis of high boiling by-products of the hydrogenation when reactivated after deactivation of the catalyst. It is another object of the present invention to provide a process for producing aromatic amines in an industrially advantageous manner using such a catalyst, which allows the long-term use of the catalyst.

As a result of extensive researches, the present inventors have found that (1) the catalyst comprising a metal catalyst component comprising Ni and/or Co and a specific amount of zirconia as a carrier component, which is prepared by drying, calcining and forming a precipitate produced by adding an aqueous solution containing soluble salts of the metal catalyst component and the carrier component to an aqueous alkali solution; and (2) the catalyst comprising the metal catalyst component and the carrier component, which is prepared by filtering a precipitate produced by adding an aqueous solution containing soluble salts of the metal catalyst component and the carrier component to an aqueous alkali solution; forming the precipitate without drying to obtain a formed product; and subjecting the formed product to drying and then calcining, are free from breaking owing to rapid generation of methane and evaporation of liquid ammonia by hydrogenolysis of high boiling by-products when reactivated after deactivation of the catalyst.

The present invention has been accomplished on the basis of the finding.

Thus, in a first aspect of the present invention, there is provided a catalyst for producing aromatic amines, comprising an effective amount of a metal catalyst component comprising Ni and/or Co; and a carrier component comprising zirconia which is present in an amount of 20 to 80% by weight based on the total weight of the catalyst, the catalyst being prepared by drying, calcining and then forming a precipitate produced by adding an aqueous solution containing a soluble salt of the metal catalyst component and a soluble salt of the carrier component to an aqueous alkali solution, or a mixture of a precipitate produced by adding an aqueous solution containing a soluble salt of the metal catalyst component to an aqueous alkali solution, and a precipitate produced by adding a soluble salt of the carrier component to an aqueous alkali solution.

In a second aspect of the present invention, there is provided a catalyst for producing aromatic amines, comprising an effective amount of a metal catalyst component comprising Ni and/or Co; and a carrier component comprising at least one material selected from the group consisting of silica, alumina, silica-alumina, titania and zirconia, the catalyst being prepared by filtering a precipitate produced by adding an aqueous solution containing a soluble salt of the metal catalyst component and a soluble salt of the carrier component to an aqueous alkali solution, or a mixture of a precipitate produced by adding an aqueous solution containing a soluble salt of the metal catalyst component to an aqueous alkali solution, and a precipitate produced by adding an aqueous solution containing a soluble salt of the carrier component to an aqueous alkali solution, the precipitate or the mixture of precipitates having a water content of 30 to 90% by weight; forming the precipitate or the mixture of precipitates without drying to obtain a formed product; and subjecting the formed product to drying and then calcining.

In a third aspect of the present invention, there is provided a process for producing aromatic amines by hydrogenating aromatic nitriles in a liquid phase using the catalyst according to any one of the first and second aspects.

DETAILED DESCRIPTION OF THE INVENTION

The catalyst for producing aromatic amines according to the first aspect of the invention comprises a metal catalyst component comprising Ni and/or Co, and a carrier component comprising zirconia, wherein the carrier component is present in an amount of 20 to 80% by weight based on the total weight of the catalyst.

The catalyst for producing aromatic amines according to the first aspect of the invention is prepared by drying, calcining and forming a precipitate (A) or a mixture of a precipitate (B) and a precipitate (C), wherein the precipitate (A) is produced by adding an aqueous solution containing a soluble salt of the metal catalyst component and a soluble salt of the carrier component to an aqueous alkali solution, the precipitate (B) is produced by adding an aqueous solution containing a soluble salt of the metal catalyst component to an aqueous alkali solution, and the precipitate (C) is produced by adding a soluble salt of the carrier component to an aqueous alkali solution.

In the catalyst of the first aspect of the present invention, the carrier component is present in an amount of 20 to 80% by weight based on the total weight of the catalyst. When the amount of the carrier component is less than 20% by weight, the catalyst suffers from breaking owing to rapid generation of methane and evaporation of liquid ammonia by hydrogenolysis of high boiling by-products of the hydrogenation when reactivated after deactivation of the catalyst. On the other hand, when the amount of the carrier component exceeds 80% by weight, the amount of the catalytically active component contained in the catalyst becomes relatively small and therefore fails to produce the aimed amine at a sufficient yield.

The catalyst for producing aromatic amines according to the second aspect of the present invention comprises a metal catalyst component comprising Ni and/or Co and a carrier component comprising at least one material selected from the group consisting of silica, alumina, silica-alumina, titania and zirconia.

The catalyst for producing aromatic amines according to the second aspect of the present invention is prepared by (1) filtering a precipitate (D) or a mixture of a precipitate (E) and a precipitate (F), wherein the precipitate (D) is produced by adding an aqueous solution containing a soluble salt of the metal catalyst component and a soluble salt of the carrier component to an aqueous alkali solution, the precipitate (E) is produced by adding an aqueous solution containing a soluble salt of the metal catalyst component to an aqueous alkali solution, and the precipitate (F) is produced by adding a soluble salt of the carrier component to an aqueous alkali solution, the precipitate or the mixture of precipitates having a water content of 30 to 90% by weight; (2) forming the precipitate (D) or the mixture of the precipitate (E) and the precipitate (F) without drying to obtain a formed product; and (3) subjecting the formed product to drying and then calcining.

In the catalyst according to the second aspect of the present invention, the carrier component is composed of a gel-formable material such as silica, alumina, silica-alumina, titania, zirconia or a combination thereof. These materials are used in the form of soluble salts thereof for the production of the catalyst.

The content of the carrier component in the catalyst according to the second aspect of the present invention is preferably 20 to 80% by weight based on the total weight of the catalyst similarly to that in the catalyst according to the first aspect of the present invention.

In the catalysts according to each of the first and second aspects of the present invention, the metal catalyst component comprises Ni and/or Co. The metal catalyst component may contain in addition to Ni and/or Co, at least one element selected from the group consisting of Li, Na, K, Rb, Cs, Be, Ca, Ba, Ti, Cu, Cr, Zn, Mn, Mg, Fe, Ga, Ge, Nb, Ru, Rh, Pd, Ir, Pt, Bi, Al, Si, In, Sr, Ce and Mo.

Soluble salts of the metal catalyst component and the carrier component are used for the preparation of the catalyst. Preferred soluble salts are acid salts. Examples of the acid salts include nitrates, sulfates, hydrochlorides, acetates, formates and the like. Of these acid salts, preferred are nitrates.

The catalyst according to the first aspect of the present invention preferably has a composition represented by the following formula:

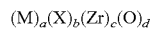

$(M)_a(X)_b(Zr)_c(O)_d$ wherein M is Ni and/or Co; X is at least one element selected from the group consisting of Li, Na, K, Rb, Cs, Be, Ca, Ba, Ti, Cu, Cr, Zn, Mn, Mg, Fe, Ga, Ge, Nb, Ru, Rh, Pd, Ir, Pt, Bi, Al, Si, In, Sr, Ce and Mo; suffixes a, b, c and d are respectively atomic ratios wherein a is 0.03 to 1.0; b is 0 to 1.0; c is 0.05 to 0.6; and d is a number of oxygen atoms bonded to Zr and bonded to X if X exists as an oxide.

In the first and second aspects of the present invention, a mixed aqueous solution containing the soluble salt of the metal catalyst component and the soluble salt of the carrier component may be added to an aqueous alkali solution so as to form a precipitate. Alternatively, an aqueous solution containing the soluble salt of the metal catalyst component and an aqueous solution containing the soluble salt of the carrier component may be respectively added to aqueous alkali solutions so as to separately form precipitates, and the thus obtained precipitates are mixed with each other to form a mixture thereof. As the aqueous alkali solution used for the precipitation, there may be used aqueous solutions containing hydroxides, carbonates or bicarbonates of alkali metals or ammonium.

In the first and second aspects of the present invention, the respective precipitates of the metal catalyst component and the carrier component, or the mixture of precipitates are prepared by co-precipitation or kneading of the respective components. For example, in the case of preparing a catalyst in which Ni is supported on a zirconia carrier, the precipitate is prepared by the following method. Namely, an aqueous solution of a nickel salt such as nickel nitrate and nickel sulfate is added to an aqueous ammonium bicarbonate solution to obtain a slurry of nickel carbonate. Then, an aqueous solution of a zirconium salt such as zirconium nitrate and zirconium sulfate and an aqueous ammonium bicarbonate solution are simultaneously poured into the slurry to precipitate zirconium carbonate in the slurry. The resulting slurry is then subjected to filtration and washing to separate the precipitate therefrom.

The catalyst according to the first aspect of the present invention is prepared by drying, calcining and then forming the thus obtained precipitate by any known industrial method. For example, there may be used a tablet press method. More specifically, the obtained precipitate is dried at a temperature of 50 to 150° C., calcined and then press-molded into tablets. Preferably, the thus obtained catalyst in tablet form has breaking strength of 15 to 30 MPa. When the breaking strength is lower than 15 MPa, the catalyst tends to suffer from breaking owing to rapid generation of methane and evaporation of liquid ammonia by hydrogenolysis of high boiling by-products of the hydrogenation when reactivated after deactivation of the catalyst. When the breaking strength exceeds 30 MPa, the catalyst is incapable of maintaining a porous structure thereof and thus fails to provide a sufficient yield of the aimed amine.

The catalyst according to the second aspect of the present invention is prepared by filtering the precipitate obtained by adding the soluble salts to the aqueous alkali solution so as to have a water content of 30 to 90% by weight, forming the thus obtained precipitate without drying to obtain a formed product, and then drying and calcining the formed product.

When the water content is more than 90% by weight, the precipitate is unable to keep its shape during the forming. On the other hand, when the water content is less than 30% by weight, the carrier component is incapable of holding a sufficient binding force. As a result, the obtained catalyst fails to have sufficient rigidity and, therefore, tends to suffer from breaking owing to rapid generation of methane and evaporation of liquid ammonia by hydrogenolysis of by-products of the hydrogenation when reactivated after deactivation of the catalyst. The catalyst attains a sufficient rigidity only when prepared by forming the precipitate with a water content of 30 to 90% by weight before the drying. If the precipitate is dried, mixed with a binder or water so as to adjust a water content of the dried precipitate to 30 to 90% by weight, and then formed, the carrier component does not keep the binding force, whereby the obtained catalyst fails to have a sufficient rigidity and tends to suffer from breaking owing to rapid generation of methane and evaporation of liquid ammonia by hydrogenolysis of by-products of the hydrogenation when reactivated after deactivation of the catalyst.

In the preparation of the catalyst according to the second aspect of the present invention, the forming is carried out by any industrially practicable wet granulation method. For example, as products formed by such a method, there may be illustrated extrusion-molded articles formed by the method reported in "Factory Operation Series: Granulation", sections 18 to 32 of "Chemical Engineering (extra number)" published by Kagaku Kogyo-sha, 1968, or molded articles formed via sizing procedure using a pulverization sizer or a spherical sizer.

The precipitate obtained after filtering in the first aspect of the present invention, or the formed product obtained without drying in the second aspect of the present invention, is dried at a temperature of 30 to 150° C., and then calcined. Meanwhile, the precipitate may be washed at any time after filtered or dried.

The calcining may be carried out by heating the dried precipitate powder in air at a temperature of 200 to 500° C., preferably 250 to 450° C., for several hours.

The thus formed catalyst is activated by hydrogen reduction, and then subjected to the hydrogenation of aromatic nitrites. The reduction is conducted by heating the catalyst under a gas flow containing 1 to 80%, preferably 1 to 60% of hydrogen and the balance being inert gas such as nitrogen at a space velocity SV of 100 to 1000 $Hr^{-1}$, at a temperature of 200 to 600° C., preferably 200 to 500° C. for several hours.

In the third aspect of the present invention, there is provided a process for producing aromatic amines by hydrogenating aromatic nitriles in liquid phase using either one of the catalysts according to the first and second aspects of the present invention.

The aromatic nitriles used in the production of aromatic amines have one or more cyano groups on an aromatic ring thereof. As such aromatic nitriles, there may be exemplified benzonitrile, phthalonitrile, isophtalonitrile, terephthalonitrile and the like.

The aromatic nitriles may have other substituents not contributing to the hydrogenation reaction such as an alkyl group, an alkoxy group, halogen, an amino group, an amide group, a hydroxyl group or the like.

Although the reactivity of aromatic nitrile in the hydrogenation reaction widely varies depending on the substituents on the aromatic ring, the aromatic nitrile having any of the above-mentioned substituents is efficiently hydrogenated in the process of the present invention.

In the process according to the third aspect of the present invention, the hydrogenation is carried out in liquid phase by dissolving the aromatic nitrile in a solvent.

As the solvent, there may be used any inert organic solvent that is not reduced with hydrogen during the reaction. Examples of the inert organic solvent include alcohols such as methanol, ethanol and propyl alcohol; hydrocarbons such as meta-xylene, mesitylene and pseudocumene; ethers such as dioxane; and the like.

In order to inhibit production of by-products during the hydrogenation, ammonia is preferably added into the inert organic solvent. For example, liquid ammonia is mixed into the inert organic solvent. The amount of the solvent used is 15 to 95 moles per one mole of the aromatic nitrile reactant. When the amount of the solvent is less than the above-specified range, the aromatic nitrile added is not sufficiently dissolved in the solvent. On the other hand, when the amount of the solvent is more than the above-specified range, the space time yield of the aimed amine is decreased.

In the process according to the third aspect of the present invention, it is not necessarily required to purify hydrogen used in the hydrogenation, and industrial grade hydrogen may be used. The partial pressure of hydrogen in the reaction system is from 3.0 to 20.0 MPa (Gauge), preferably from 4.0 to 15.0 MPa (Gauge). When the partial pressure of hydrogen is lower than the above-specified range, the yield of the aimed amine becomes insufficient. When the partial pressure of hydrogen is higher than the above-specified range, a specific high-pressure reactor is needed, leading to increase in cost.

The hydrogenation in the process according to the third aspect of the present invention may be conducted by any suitable method such as a batch method or a flow method. The reaction temperature is 20 to 200° C., preferably 40 to 180° C. When the reaction temperature is lower than 20° C., the conversion rate of the aromatic nitrile becomes low. When the reaction temperature is higher than 200° C., the yield of the aimed amine decreases with increase in the amount of by-products having boiling points higher than that of the aimed amine.

The contact time for contacting the solution with the catalyst varies depending on the kind of nitrile, the ratio between nitrile, solvent and hydrogen charged, the reaction temperature and the reaction pressure, and is usually 0.1 to 5.0 hours.

The aromatic amine produced in the process according to the third aspect of the present invention may be separated and collected from the solvent by any known method. For example, the reaction system is separated into a liquid component and a gas component, and then the liquid component is distilled away to obtain the aimed amine product.

As described above, when aromatic nitriles are hydrogenated into aromatic amines using either one of the catalysts according to the first and second aspects of the present invention, the catalyst is inhibited from suffering from breaking owing to rapid generation of methane gas and evaporation of liquid ammonia by hydrogenolysis of high boiling by-products of the hydrogenation when reactivated after deactivation of the catalyst, and is therefore usable over a long period of time.

Thus, in accordance with the present invention, it is possible to produce aromatic amines from aromatic nitrites in an extremely industrially advantageous manner.

EXAMPLES

The present invention will be described in more detail with reference to the following examples. However, it should be noted that the following examples are only illustrative and not intended to limit the invention thereto.

In the following examples, the catalysts prepared were subjected to the break test as well as the activity test as described below by application examples. That is, a 100-ml autoclave was charged with 50 tablets of the catalyst and 10 g of liquid ammonia, heated up to 120° C., and allowed to stand for 18 hours. The tablets of the catalyst were taken out of the autoclave, and the degree of break of the catalyst tablets was evaluated.

Example 1

First Aspect of the Invention

Into 840 g of 40° C. pure water were dissolved 305.0 g of nickel nitrate hexahydrate: $Ni(NO_3)_2.6H_2O$ and 13.6 g of cobalt nitrate hexahydrate: $Co(NO_3)_2.6H_2O$ to prepare an aqueous mixed metal salt solution. Also, 190.6 g of ammonium bicarbonate: $NH_4HCO_3$ was dissolved in 2.4 kg of pure water, and the resulting aqueous ammonium bicarbonate solution was heated up to 40° C. with intimately stirring. Then, the aqueous mixed metal salt solution maintained at 40° C. was added while stirring to the aqueous ammonium bicarbonate solution to obtain a slurry of nickel carbonate. The obtained slurry was heated up to 80° C., held for 30 minutes at 80° C., cooled to 40° C., and then held at the same temperature. Subsequently, 118.4 g of an aqueous solution containing zirconium nitrate in an amount of 25% by weight in terms of $ZrO_2$ was mixed with 300 g of pure water, and the resulting mixture was held at 40° C. Further, 42.8 g of ammonium bicarbonate: $NH_4HCO_3$ was dissolved in 530 g of pure water, and the resulting solution was held at 40° C. The aqueous zirconium nitrate solution and the aqueous ammonium bicarbonate solution were simultaneously poured into the slurry to precipitate zirconium carbonate in the slurry. The resultant slurry was stirred at 40° C. for 30 minutes, filtered and washed to separate a precipitate therefrom. The precipitate was dried at 110° C. for one night, and calcined in air at 380° C. for 18 hours. The calcined precipitate powder was mixed with 3% by weight graphite. The mixture was press-formed into tablets (3.0 mmφ×2.5 mm). The catalyst tablets were reduced in a hydrogen gas flow at 400° C. It was confirmed that the thus obtained catalyst tablets had a breaking strength of 22.2 MPa.

Further, it was confirmed that the catalyst tablets were free from crack and split when subjected to the break test.

Application Example 1

A 100-ml autoclave was charged with 3.2 g of isophtalonitrile, 10.4 g of mesitylene, 10.0 g of liquid ammonia and 2.0 g of the catalyst prepared in EXAMPLE 1. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 99.4 mol %; and the yield of m-xylenediamine was 82.0 mol %.

Application Example 2

A 100-ml autoclave was charged with 3.2 g of terephtalonitrile, 10.4 g of mesitylene, 10.0 g of liquid ammonia and 2.0 g of the catalyst prepared in EXAMPLE 1. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephtalonitrile was 99.7 mol %; and the yield of p-xylenediamine was 84.3 mol %.

Example 2

First Aspect of the Invention

Into 1 kg of 40° C. pure water were dissolved 353.1 g of nickel nitrate hexahydrate: $Ni(NO_3)_2.6H_2O$ to prepare an aqueous nickel nitrate solution. Also, 211.2 g of ammonium bicarbonate: $NH_4HCO_3$ was dissolved in 1 kg of pure water, and the resulting aqueous ammonium bicarbonate solution was heated up to 40° C. while intimately stirring. Then, the aqueous nickel nitrate solution maintained at 40° C. was added, with stirring, to the aqueous ammonium bicarbonate solution, thereby obtaining a slurry containing precipitated nickel carbonate. The obtained slurry was heated up to 80° C., and kept for 30 minutes at 80° C., cooled down to 40° C., and then held at the same temperature. Further, 151.9 g of an aqueous solution containing zirconium nitrate in an amount of 25% by weight in terms of $ZrO_2$ was mixed with 382.8 g of pure water, and the resulting mixture was held at 40° C. In addition, 54.9 g of ammonium bicarbonate: $NH_4HCO_3$ was dissolved in 679.9 g of pure water, and the resulting solution was held at 40° C. The aqueous zirconium nitrate solution and the aqueous ammonium bicarbonate solution were simultaneously poured into the slurry to precipitate zirconium carbonate. The resultant slurry was stirred at 40° C. for 30 minutes, and filtered and washed to separate a precipitate therefrom. The obtained precipitate was dried at 110° C. for one night, and calcined in air at 380° C. for 18 hours. The calcined precipitate powder was mixed with 3% by weight graphite. The mixture was press-formed into tablets (3.0 mmφ×2.5 mm). The catalyst tablets were reduced in a hydrogen gas flow at 400° C. It was confirmed that the thus obtained catalyst tablets had a breaking strength of 29.1 MPa. Further, it was confirmed that the catalyst tablets were free from crack and split when subjected to the break test.

Application Example 3

A 100-ml autoclave was charged with 3.2 g of isophtalonitrile, 10.4 g of mesitylene, 10.0 g of liquid ammonia and 2.0 g of the catalyst prepared in EXAMPLE 2. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 99.1 mol %; and the yield of m-xylenediamine was 79.3 mol %.

Application Example 4

A 100-ml autoclave was charged with 3.2 g of terephtalonitrile, 10.4 g of mesitylene, 10.0 g of liquid ammonia and 2.0 g of the catalyst prepared in EXAMPLE 2. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.4 mol %; and the yield of p-xylenediamine was 81.2 mol %.

Comparative Example 1

After dissolving 305.0 g of nickel nitrate hexahydrate: $Ni(NO_3)_2.6H_2O$, 6.5 g of copper nitrate trihydrate: $Cu(NO_3)_2.3H_2O$, and 7.1 g of chrome nitrate nonahydrate:

Cr(NO$_3$)$_3$·9H$_2$O in 1 kg of 40° C. pure water, the resulting solution was mixed with 29.6 g of diatom earth while stirring at 40° C. Into the thus obtained suspension, an aqueous solution prepared by dissolving 128.6 g of sodium carbonate: Na$_2$CO$_3$ in 1 kg of 40° C. pure water was poured while stirring, thereby obtaining a slurry. The slurry was heated up to 80° C. and kept for 30 minutes at 80° C. Then, the slurry was filtered and washed to obtain a precipitate. The precipitate was dried at 110° C. for one night, and calcined in air at 380° C. for 18 hours. The calcined precipitate powder was mixed with 3% by weight graphite. The mixture was press-formed into tablets (3.0 mmφ×2.5 mm). The catalyst tablets were reduced in a hydrogen gas flow at 400° C. It was confirmed that the thus obtained catalyst tablets had a breaking strength of 16.3 MPa. Further, it was confirmed that 28 out of 50 catalyst tablets were cracked or split when subjected to the break test.

Comparative Application Example 1

A 100-ml autoclave was charged with 3.2 g of isophthalonitrile, 10.4 g of mesitylene, 10.0 g of liquid ammonia and 2.0 g of the catalyst prepared in COMPARATIVE EXAMPLE 1. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 99.5 mol %; and the yield of m-xylenediamine was 80.6 mol %.

Comparative Application Example 2

A 100-ml autoclave was charged with 3.2 g of terephthalonitrile, 10.4 g of mesitylene, 10.0 g of liquid ammonia and 2.0 g of the catalyst prepared in COMPARATIVE EXAMPLE 1. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.7 mol %; and the yield of p-xylenediamine was 81.3 mol %.

Example 3

Second Aspect of the Invention

Into 1.8 kg of pure water was dissolved 251.6 g of ammonium bicarbonate: NH$_4$HCO$_3$, and the resulting ammonium bicarbonate solution was heated up to 40° C. while intimately stirring. Further, 255.1 g of nickel nitrate hexahydrate Ni(NO$_3$)$_2$·6H$_2$O, 15.0 g of copper nitrate trihydrate: Cu(NO$_3$)$_2$·3H$_2$O, 30.3 g of chrome nitrate nonahydrate: Cr(NO3)$_3$·9H$_2$O, and 189.3 g of an aqueous solution containing zirconium nitrate in an amount of 25% by weight in terms of ZrO$_2$ were dissolved in 1.5 kg of 40° C. pure water to prepare an aqueous mixed metal salt solution. The aqueous mixed metal salt solution maintained at 40°C. was added while intimately stirring to the aqueous ammonium bicarbonate solution at 40° C., thereby obtaining a slurry. After heated up to 80° C. and kept for 30 minutes at 80° C., the slurry was filtered and washed to obtain a precipitate with a water content of 70% by weight. The precipitate was extruded into tablets (3.0 mmφ). The tablets were dried at 110° C. for one night, and calcined in air at 380° C. for 18 hours. The thus obtained catalyst tablets were reduced in a hydrogen gas flow at 400° C. It was confirmed that the catalyst tablets were free from crack and split when subjected to the break test.

Application Example 5

A 100-ml autoclave was charged with 3.2 g of isophthalonitrile, 10.4 g of mesitylene, 10.0 g of liquid ammonia and 2.0 g of the catalyst prepared in EXAMPLE 3. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 99.3 mol %; and the yield of m-xylenediamine was 78.6 mol %.

Application Example 6

A 100-ml autoclave was charged with 3.2 g of terephthalonitrile, 10.4 g of mesitylene, 10.0 g of liquid ammonia and 2.0 g of the catalyst prepared in EXAMPLE 3. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.4 mol %; and the yield of p-xylenediamine was 81.2 mol %.

Example 4

Second Aspect of the Invention

Into 1.4 kg of pure water was dissolved 168.7 g of sodium carbonate: Na$_2$CO$_3$, and the resulting solution was heated up to 40° C. while intimately stirring. Further, 255.1 g of nickel nitrate hexahydrate: Ni(NO$_3$)$_2$·6H$_2$O, 15.0 g of copper nitrate trihydrate: Cu(NO$_3$)$_2$·3H$_2$O, 30.3 g of chrome nitrate nonahydrate: Cr(NO$_3$)$_3$·9H$_2$O, and 189.3 g of an aqueous solution containing zirconium nitrate in an amount of 25% by weight in terms of ZrO$_2$ were dissolved in 1.5 kg of 40° C. pure water to prepare an aqueous mixed metal salt solution. The aqueous mixed metal salt solution maintained at 40° C. was added while intimately stirring to the aqueous ammonium bicarbonate solution at 40° C., thereby obtaining a slurry. After heated up to 80° C. and kept for 30 minutes at 80° C., the slurry was filtered and washed to obtain a precipitate with a water content of 74% by weight. The precipitate was extruded into tablets (3.0 mmφ). The tablets were dried at 110° C. for one night, and calcined in air at 380° C. for 18 hours. The thus obtained catalyst tablets were reduced in a hydrogen gas flow at 400° C. It was confirmed that the catalyst tablets were free from crack and split when subjected to the break test.

Application Example 7

A 100-ml autoclave was charged with 3.2 g of isophthalonitrile, 10.4 g of mesitylene, 10.0 g of liquid ammonia and 2.0 g of the catalyst prepared in EXAMPLE 4. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 99.0 mol %; and the yield of m-xylenediamine was 77.3 mol %.

Application Example 8

A 100-ml autoclave was charged with 3.2 g of terephthalonitrile, 10.4 g of mesitylene, 10.0 g of liquid ammonia and 2.0 g of the catalyst prepared in EXAMPLE 4. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.7 mol %; and the yield of p-xylenediamine was 80.6 mol %.

Example 5

Second Aspect of the Invention

Into 1.0 kg of pure water was dissolved 47.84 g of ammonium bicarbonate: $NH_4HCO_3$, and the resulting solution was heated up to 40° C. while intimately stirring. Further, 160.0 g of nickel nitrate hexahydrate: $Ni(NO_3)_2.6H_2O$ was dissolved in 1.0 kg of 40° C. pure water to prepare an aqueous metal salt solution. The aqueous metal salt solution maintained at 40° C. was added while intimately stirring to the aqueous ammonium bicarbonate solution at 40° C., thereby obtaining a slurry of nickel carbonate. Further, 57.68 g of sodium silicate which contains $SiO_2$ 56.0% by weight and NaO 20.0% by weight was dissolved into 608 g of 40° C. pure water. Aqueous nitric acid was prepared by dissolving 38.21 g of nitric acid which contains $HNO_3$ 61.0% by weight into 344 g of 40° C. pure water. This aqueous ammonium bicarbonate solution and aqueous nitric acid were added to the slurry of nickel carbonate simultaneously to precipitate silica. After heated up to 80° C. and kept for 30 minutes at 80° C., the slurry was filtered and washed to obtain a precipitate with a water content of 87% by weight. The precipitate was extruded into tablets (3.0 mmφ). The tablets were dried at 110° C. for one night, and calcined in air at 380° C. for 18 hours. The thus obtained catalyst tablets were reduced in a hydrogen gas flow at 400° C. It was confirmed that the catalyst tablets were free from crack and split when subjected to the break test.

Application Example 9

A 100-ml autoclave was charged with 3.2 g of isophthalonitrile, 10.4 g of mesitylene, 10.0 g of liquid ammonia and 2.0 g of the catalyst prepared in EXAMPLE 5. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 98.7 mol %; and the yield of m-xylenediamine was 79.6 mol %.

Application Example 10

A 100-ml autoclave was charged with 3.2 g of terephthalonitrile, 10.4 g of mesitylene, 10.0 g of liquid ammonia and 2.0 g of the catalyst prepared in EXAMPLE 5. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.9 mol %; and the yield of p-xylenediamine was 81.2 mol %.

Comparative Example 2

A slurry was prepared in the same manner as in EXAMPLE 3, and filtered and washed to obtain a precipitate. The precipitate was then filtered by suction so as to adjust a water content thereof to 20% by weight. The precipitate was extruded into tablets (3.0 mmφ). The obtained tablets were dried at 110° C. for one night, and calcined in air at 380° C. for 18 hours. The thus obtained catalyst tablets were reduced in a hydrogen gas flow at 400° C. It was confirmed that 35 out of 50 catalyst tablets were cracked or split when subjected to the break test.

Comparative Application Example 3

A 100-ml autoclave was charged with 3.2 g of isophthalonitrile, 10.4 g of mesitylene, 10.0 g of liquid ammonia and 2.0 g of the catalyst prepared in COMPARATIVE EXAMPLE 2. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of isophtalonitrile was 99.3 mol %; and the yield of m-xylenediamine was 78.3 mol %.

Comparative Application Example 4

A 100-ml autoclave was charged with 3.2 g of terephthalonitrile, 10.4 g of mesitylene, 10.0 g of liquid ammonia and 2.0 g of the catalyst prepared in COMPARATIVE EXAMPLE 2. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.8 mol %; and the yield of p-xylenediamine was 82.3 mol %.

Comparative Example 3

A slurry was prepared in the same manner as in EXAMPLE 3, and filtered and washed to obtain a precipitate. The precipitate was dried until the water content thereof reached 10% by weight. The dried precipitate was mixed with water to adjust a water content thereof to 70% by weight, and then extruded into tablets (3.0 mmφ). The obtained tablets were dried at 110° C. for one night, and calcined in air at 380° C. for 18 hours. The thus obtained catalyst tablets were reduced in a hydrogen gas flow at 400° C. It was confirmed that 20 out of 50 catalyst tablets were cracked or split when subjected to the break test.

Comparative Application Example 5

A 100-ml autoclave was charged with 3.2 g of isophthalonitrile, 10.4 g of mesitylene, 10.0 g of liquid ammonia and 2.0 g of the catalyst prepared in COMPARATIVE EXAMPLE 3. Then, a hydrogen gas was introduced into the autoclave until the total pressure reached 10.8 MPa (Gauge).

The autoclave was shaken at 120° C. until no pressure change was observed. The reaction solution was taken out of the autoclave, and analyzed. As a result of the analysis, it was confirmed that the conversion rate of isophtalonitrile was 99.0 mol %; and the yield of m-xylenediamine was 79.2 mol %.

Comparative Application Example 6

A 100-ml autoclave was charged with 3.2 g of terephthalonitrile, 10.4 g of mesitylene, 10.0 g of liquid ammonia and 2.0 g of the catalyst prepared in COMPARATIVE EXAMPLE 3. Then, a hydrogen gas was introduced into the autoclave until the total pressure reached 10.8 MPa (Gauge). The autoclave was shaken at 120° C. until no pressure change was observed. The reaction solution was taken out of the autoclave, and analyzed. As a result of the analysis, it was confirmed that the conversion rate of terephthalonitrile was 99.9 mol %; and the yield of p-xylenediamine was 81.1 mol %.

What is claimed is:

1. A catalyst, capable of being used as a catalyst in producing aromatic amines, having the following composition:

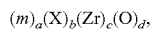

wherein M is Ni and/or Co; X is at least one element selected from the group consisting of Li, Na, K, Rb, Cs, Be, Ca, Ba, Ti, Cu, Cr, Zn, Mn, Mg, Fe, Ga, Ge, Nb, Ru, Rh, Pd, Ir, Pt, Bi, Al, Si, In, Sr, Ce and Mo; and a, b, c and d respectively are atomic ratios wherein a is 0.03 to 1.0, b is 0 to 1.0, c is 0.05 to 0.6, and d is a number of oxygen atoms bonded to Zr and to X when X is an oxide, with zirconia being included as a carrier component, wherein the catalyst is prepared by drying, calcining and reducing a precipitate produced by adding an aqueous solution containing a soluble salt of the metal catalyst component and a soluble salt of the carrier component to an aqueous alkali solution, or a mixture of a precipitate produced by adding an aqueous solution containing a soluble salt of the metal catalyst component to an aqueous alkali solution, and a precipitate produced by adding a soluble salt of the carrier component to an aqueous alkali solution, and then forming the dried, calcined and reduced precipitate into the catalyst.

2. The catalyst according to claim 1, wherein the forming is conducted by a tablet press method such that the catalyst has a breaking strength of 15 to 30 MPa.

3. The catalyst according to claim 1, wherein said aqueous alkali solution is an aqueous solution containing hydroxides, carbonates or bicarbonates of alkali metals or ammonium.

4. The catalyst according to claim 1, wherein the drying has been performed at a temperature of 30° to 150° C., the calcining has been performed at a temperature of 200° to 500° C., and the reducing has been performed at a temperature of 200° to 600° C.

5. The catalyst according to claim 1, which is free from breaking owing to rapid generation of methane and evaporation of liquid ammonia by hydrogenolysis of high-boiling by-products upon reactivation after deactivation of the catalyst.

6. A catalyst, capable of being used as a catalyst in producing aromatic amines, having the following composition:

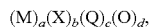

wherein M is Ni and/or Co, X is at least one element selected from the group consisting of Li, Na, K, Rb, Cs, Be, Ca, Ba, Ti, Cu, Cr, Zn, Mn, Mg, Fe, Ga, Ge, Nb, Ru, Rh, Pd, Ir, Pt, Bi, Al, Si, In, Sr, Ce and Mo; Q is at least one member selected from the group consisting of silica, alumina, silica-alumina and zirconia; and a, b, c and d respectively are atomic ratios wherein a is 0.03 to 1.0, b is 0 to 1.0, c is 0.05 to 0.6; and d is a number of oxygen atoms bonded to Q and bonded to X if X exists as an oxide, with Q being included as a carrier component, wherein the catalyst is prepared by filtering a precipitate produced by adding an aqueous solution containing a soluble salt of the metal catalyst component and a soluble salt of the carrier component to an aqueous alkali solution, or a mixture of a precipitate produced by adding an aqueous solution containing a soluble salt of the metal catalyst component to an aqueous alkali solution, and a precipitate produced by adding an aqueous solution containing a soluble salt of the carrier component to an aqueous alkali solution, the precipitate or the mixture of precipitates having a water content of 30 to 90% by weight; forming the precipitate or the mixture of precipitates without drying to obtain a formed product; and subjecting the formed product to drying and then calcining.

7. The catalyst according to claim 6, wherein the forming is conducted by wet granulation.

8. The catalyst according to any one of claims 1 to 7, wherein the catalyst is prepared by using in addition to (1) soluble salts of Ni and/or Co, (2) a soluble salt of X where the catalyst includes X.

9. The catalyst according to claim 8, wherein the soluble salts of the metal catalyst component and the carrier component are acid salts.

10. The catalyst according to claim 9, wherein said acid salts are nitrates.

11. The catalyst according to claim 7, wherein the soluble salts of M, X, where the catalyst includes X, and the carrier component are acid salts.

12. The catalyst according to claim 11, wherein said acid salts are nitrates.

13. The catalyst according to claim 6, wherein said aqueous alkali solution is an aqueous solution containing hydroxides, carbonates or bicarbonates of alkali metals or ammonium.

14. The catalyst according to claim 6, wherein the drying has been performed at a temperature of 30° to 150° C., and the calcining has been performed at a temperature of 200° to 500° C.

15. The catalyst according to claim 6, which is free from breaking owing to rapid generation of methane and evaporation of liquid ammonia by hydrogenolysis of high-boiling by-products upon reactivation after deactivation of the catalyst.

16. The catalyst according to claim 6, wherein said carrier component is present in an amount of 20% to 80% by weight based on the total weight of the catalyst.

17. The catalyst according to claim 6, wherein Q is at least zirconia.

18. The catalyst according to any one of claims 1 to 7, wherein the catalyst includes X.

19. The catalyst according to claim 18, wherein the catalyst is prepared by using in addition to (1) soluble salts of Ni and/or Co, (2) a soluble salt of X.

20. The catalyst according to claim 6, wherein Q is zirconia, and the carrier component further includes at least one of silica, alumina, and silicon-alumina.

21. A catalyst having the following composition:

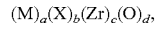

wherein M is Ni and/or Co; X is at least one element selected from the group consisting of Li, Na, K, Rb, Cs, Be, Ca, Ba, Ti, Cu, Cr, Zn, Mn, Mg, Fe, Ga, Ge, Nb, Ru, Rh, Pd, Ir, Pt, Bi, Al, Si, In, Sr, Ce and Mo; and a, b, c and d respectively are atomic ratios wherein a is 0.03 to 1.0, b is 0 to 1.0, c is 0.05 to 0.6, and d is a number of oxygen atoms bonded to Zr and to X when X is an oxide, with zirconia being included as a carrier component, wherein the catalyst is prepared by drying, calcining and reducing a precipitate produced by adding an aqueous solution containing a soluble salt of the metal catalyst component and a soluble salt of the carrier component to an aqueous alkali solution, or a mixture of a precipitate produced by adding an aqueous solution containing a soluble salt of the metal catalyst component to an aqueous alkali solution, and a precipitate produced by adding a soluble salt of the carrier component to an aqueous alkali solution, and then forming the dried, calcined and reduced precipitate into the catalyst, and wherein the catalyst has properties such that it is used for catalyzing production of aromatic amines.

* * * * *